US007189554B2

(12) United States Patent
Apicella et al.

(10) Patent No.: US 7,189,554 B2
(45) Date of Patent: *Mar. 13, 2007

(54) TWO-COMPONENT SYSTEM THAT CONTROLS BACTERIAL MEMBRANE SYNTHESIS

(75) Inventors: Michael A. Apicella, Solon, IA (US); Andrew Preston, Cambridge (GB)

(73) Assignee: University of Iowa Research Foundation, Iowa City, IA (US)

( * ) Notice: Subject to any disclaimer, the term of this patent is extended or adjusted under 35 U.S.C. 154(b) by 511 days.

This patent is subject to a terminal disclaimer.

(21) Appl. No.: 10/288,986

(22) Filed: Nov. 5, 2002

(65) Prior Publication Data

US 2003/0104502 A1 Jun. 5, 2003

Related U.S. Application Data

(63) Continuation of application No. 09/439,226, filed on Nov. 12, 1999, now Pat. No. 6,518,037.

(51) Int. Cl.
*C12N 1/21* (2006.01)
(52) U.S. Cl. .............................. 435/252.3; 435/320.1; 435/252.33; 536/24.1
(58) Field of Classification Search ...................... None
See application file for complete search history.

(56) References Cited

U.S. PATENT DOCUMENTS

| 4,446,230 | A | 5/1984 | Zubrycki |
| 5,532,124 | A | 7/1996 | Block et al. |
| 5,705,367 | A | 1/1998 | Gotschlich ................. 435/97 |
| 5,747,276 | A | 5/1998 | Hoch et al. |
| 5,789,173 | A | 8/1998 | Peck et al. |
| 5,902,586 | A | 5/1999 | Jennings et al. |
| 6,180,111 | B1 | 1/2001 | Stein et al. |
| 6,518,037 | B2 | 2/2003 | Apicella et al. |

FOREIGN PATENT DOCUMENTS

| WO | WO-98/17805 | 4/1998 |
| WO | WO 98/17805 | 4/1998 |
| WO | WO-99/59625 | 11/1999 |
| WO | WO 99/59625 | 11/1999 |

OTHER PUBLICATIONS

Andersen et al., Loss of endotoxin liberation in *Neisseria meningitides, Acta. Path. Microbiol. Scand. Sect. B*, 89:271-278. 1981.
Brandtzaeg, P.,et al., "Plasma Endotoxin as a Predictor of Multiple Organ Failure and Death in Systemic Meningococcal Disease", *The Journal of Infectious Diseases*, 159(2), 195-204, (Feb. 1989).
Evans, B.A., "Ultrastructural Study of Cervical Gonorrhea", *The Journal of Infectious Diseases*, 136(2), 248-255, (Aug. 1977).
Galanos, C., et al., "A New Method for the Extraction of R Lipopolysaccharides", *Eur. J. Biochem*, (9), 245-249 (1969).

Lee, N., et al., "Mutation of the htrB Locus of *Haemophilus influenzae* Nontypable Strain 2019 Is Associated with Modifications of Lipid A and Phosphorylation of the Lipo-oligosaccharide", *J. Biol. Chem.*, 270(45), 27151-27159, (1995).
Wren, B.W., et al., "Degenerate PCR Primers for the Amplificatino of Fragments from Genes Encoding Response Regulators from a Range of Pathogenic Bacteria", *FEMS Microbiol. Letters*, 99, 287-291, (1992).
Zhou, D., et al., Plasmids with Erythromycin Resistance and Catechol 2, 3-dioxygenase- or beta-galactosidase-Encoding Gene Cassettes for use in *Neisseria spp.*, *Gene*, 171, 133-134, (1996).
Bulygin, V.V., et al., "Rotation of the ϵ Subunit during Catalysis by *Escherichia coli* $F_0F_1$-ATP Synthase", *J. Biol. Chem.*, 274, 31765-31769 (1998).
Meadow, P.M., et al., "The Effect of Lipopolysaccharide Composition on the Ultrastructure of *Pseudomonas aeruginosa*", *J. Gen. Microbiol.*, 105, 23-28 (1978).
Preston, A, et al., "A Two-Component Regulatory System Involved in Los Microheterogeneity in *Neisseria gonorrhose*", *Abstract Gral. Meet. Asm.*, 96, 208 (1996).
Pettit., R.K., et al., "Characterization of Naturally Elaborated Blebs from Serum-Susceptible and Serum-Resistant Strains of *Neisseria gonorrhoes*", *Mol. Microbiol.*, 6, 723-728 (1992).
Ramirez-Arcos, S., et al., "Expression and Interaction of the *minCDE* Genes of *Neisseria hgonorrhoeae*", *Abstracts Gral. Meet. Asm.*, 99, 352 (1999).
Suzuki, H., et al., "Murein-Lipoprotein of *Escherichia coli*: a protein involved in the stabilization of bacterial cell envelope", *Mol Gen. Genet.*, 167, 1-9 (1978).
Watnick, R.S., et al., *Escherichia coli* NusA is Required for Efficient RNA Binding by Phase HK022 Nun Protein, *PNAS*, 95, 1546-1551 (1998).
Zhou, D., et al., "Lipoollgosaccharide Biosynthesis in *Neisseria gonorrhoeae*: Cloning, Identification and Characterization of the α1,5 Heptosyltransferase I gene (rfaC)", *Molecular Microbio.*, 14, 609-618 (1994).
Pettit, R.K., et al., The interaction of naturally elaborated blebs from serum-susceptible and serum-resistant strains of *Neisseria gonorrhoeae* with normal human serum, *Molecular Microbiology*, 6 (6), 729-734 (1992).
Dorward, D.W., et al., DNA-binding proteins in cells and membrane blebs of *Neisseria gonorrhoeae*, *Journal of Bacteriology*, 171(8), 4196-4201 (1989).
Andersen, B.M. et al., Loss of endotoxin liberation in *Neisseria meningitides*, Acta path. Microbiol. Scand. Sec. B, 89, 271-278 (1981).

(Continued)

*Primary Examiner*—James Ketter
(74) *Attorney, Agent, or Firm*—Viksnins Harris & Padys PLLP (57) ABSTRACT

The present invention discloses a mutant *Neisseria* having extensive membrane blebbing, both an indicium and a cause of virulence in the gonococcus and meningococcus. Methods are disclosed for making and characterizing the mutant, bmrRS. Methods are disclosed for isolating bmrRS membranes for use as a vaccine. Methods are also disclosed for the use of the mutant for determining the virulence of clinical samples of *N. gonorrhoeae* and *N. meningitidis*. Methods are also disclosed for the screening of antibiotics targeted to virulent *Neisseria*.

20 Claims, 4 Drawing Sheets

OTHER PUBLICATIONS

Andersen, B..M. ,et al. ,"Loss of Endotoxin Liberation in *Neisseria meningitidis*", *Acta Path. Microbiol. Scand. Sect. B*, 89, (1981),271-278.

Brandtzaeg, Peter.,et al. ,"Plasma Endotoxin as a Predictor of Multiple Organ Failure and Death in Systemic Meningococcal Disease", *The Journal of Infectious Diseases*, 159(2), (Feb. 1989), 195-204.

Bulygin, Vladimir.V. ,et al. ,"Rotation of the e Subunit during catalysis by *Escherichia coli* FoF1-ATP synthase", *J. Biol. Chem.*, 273, (Nov. 27, 1998),31765-31769.

Dorward, D..W. ,et al. ,"DNA-Binding Proteins in Cells and Membrane Blebs of *Neisseria gonorrhoeae*", *Journal of Bacteriology*, 171, (Aug. 1989),4196-4201.

Evans, Brain.A. ,"Ultrastructural Study of Cervical Gonorrhea", *The Journal of Infectious Diseases*, 136(2), (Aug. 1977),248-255.

Galanos, C..,et al. ,"A New Method for the Extraction of R Lipopolysaccharides", *Eur. J. Biochem.*, (9), (1969),245-249.

Lee, Na-Gyong.,et al. ,"Mutation of the htrB Locus of *Haemophilus influenzae* Nontypable Strain 2019 Is Associated with Modifications of Lipid A and Phosphorylation of the Lipo-oligosaccharide", *J. Biol. Chem.*, 270(45), (1995),27151-27159.

Marit, B..,et al. ,"Loss of Endotoxin Liberation in *Neisseria meningitidis*", *Acta. Path. Microbiol. Scand. Sect. B.*, 89, (1981),271-278.

Meadow, Pauline.M. ,et al. ,"The Effect of Lipopolysaccharide composition on the ultrastructure of *Pseudomonas aeruginosa*", *J. Gen. Microbiol.*, 105, (1978),23-28.

Peston, A..,et al. ,"A Two-Component Regulatory System involved in LOS Microheterogeneity in *Neisseria gonorrhoese*", *Abstracts Gral. Meet. Asm.*, 96, (1996),208.

Pettit, Robin.K. ,et al. ,"Characterization of naturally elaborated blebs from serum-susceptible and serum-resistant strains of *Neisseria gonorrhoese*", *Mol. Microbiol.*, 6, (1992),723-728.

Pettit, R..K. ,et al. ,"The Interaction of Naturally Elaborated Blebs from Serum-Susceptible and Serum-Resistant Strains of *Neisseria gonorrhoeae* with Normal Human Serum", *Molecular Microbiology*, 6, (1992),729-734.

Ramirez-Arcos, S..,et al. ,"Expression and interaction of theminCDE genes of *Neisseria gonorrhoeae*", *Abstracts Gral. Meet. Asm.*, 99, (Jun. 1999),352.

Suzuki, Hideho.,et al. ,"Murein-Lipoprotein of *Escherichia coli*: a protein involved in the stabilization of bacterial cell envelope", *Mol. Gen. Genet.*, 167, (1978),1-9.

Watnick, Randolph.S. ,et al. ,"*Escherichia coli* NusA is required for efficient RNA binding by phase HK022 Nun protein", *PNAS*, 95, (Feb. 1998),1546-1551.

Wren, Brendan.W. ,et al. ,"Degenerate PCR Primers for the Amplification of Fragments from Genes Encoding Response Regulators from a Range of Pathogenic Bacteria", *FEMS Microbiol. Letters*, 99, (1992),287-291.

Zhou, Daoguo.,et al. ,"Lipoollgosaccharide biosynthesis in *Neisseria gonorrhoese*: cloning, identification and characterization of the a1,5 heptosyltransferase I gene (rfaC)", *Molecular Microbio.*, 14, (1994),609-618.

Zhou, Dauguo.,et al. ,"Plasmids with Erythromycin Resistance and Catechol 2,3-dioxygenase- or beta-galactosidase-Encoding Gene Cassettes for use in *Neisseria spp.*", *Gene*, 171, (1996), 133-134.

Fig. 1

BASR

```
                                             AAA AAQPYDLMLL
NM: MRVLLVEDDA MIAEAVSASL KDGGYAVDWV KNGARLPLPS LMT*......
GC: MRVLLVEDDA MIA*AVSASL KDGGYAVDWV KNGAQVAAAA AAQPYDLMLL
NC: MRVLLVEDDA MIAEAVSANL KDGGYAVDWV KNGAQVAAAA AAQPYDLMLL

DLGLLGRDGL DV
NM:             MFVPL(BasS)...
GC: DLGLPGRDGL DVLSEIRAAG CTVPVLIVTA RDDLYSRLNG LDGGADDYIV
NC: DLGLPGRDGL DVLSEIRAAG CTVPVLIVTA RDDLYSRLNG LDGGADDYIV

GC: KPFDMAEFKA RMRAVLRRGS GQAQACLSNG ALSLNPATYQ VEIIAEGRQV
NC: KPFDMAELKA RMRAVLRRGS GQAQACLSNG ALSLNPATYQ VEIIAERRQV

GC: ALSNQEFSVL QALLARPGVI LSRSDSEDKV YGWGGEVESN AVDFLIHGLC
NC: ALSNKEFAVL QALLARPGVI LSRSDLEDKI YGWGAEVESN AVDFLIHALR

GC: KKLGKESIQN VRGVGWLMPR QDAV*
NC: KKLGKENIQN VRGVGWLVPG AV*
```

BASS
```
NM:                      MFVPLAM LAGMFSYYET FHETEALQDD
GC: MPDRFFKILK HSLQVRISLA LIWMFVPLAM LAGMFSYYET FHETEALQDD
NC: MLNRLIRMLK QSLQVRICIA LILMFLPLAM VAGVFSYYDT FHEAEELQDD

NM: LLRQAALYVA PDSKPETLPE GDGDTRIFVQ MPQQEDPVVS LPAHLADGLH
GC: LLRQAALYVG PDSKSETLPE GDGDTRILVQ MPQQEDPVVS LPAHLADGLH
NC: LLRQTALYVG PDYHPDALPE GDGDTRILVQ MPDQE.PIVS LPMHLKDGLH

NM: TLQADGDDDY YRVYIRTTEQ GRIAVMQENE YREDLAADAA RQSVLPLLAA
GC: TLRADGDDDY YRAYIRTTEQ GRIAVMQENE YREDLAEDAA RQSVLPLLAA
NC: TLRADEDDDY YRVYIRTTGR GRIAVMQENE YREDLAADAA MQSVLPLLAA

NM: LPLMILLTVW ITHKAMRPVR KLSQSLEQRR INDLSALSVD NIPSEIRGFV
GC: LPLMILLTVW ITHKAMRPVR KLSQSLEQRR INGLPALSVY NIPSEIRGFV
NC: LPLIILLTVW ITHQAMRPVR ILSQNLEQRR LDDLSALNTD NIPSEIKGFV

NM: TAINLLLKRA DEDIRHRQRF VADAAHELRT PMTALSLQAE RLNNMSLPPD
GC: TAINLLLKRV DEDIRRRQRF VADAAHELRT PMTALSLQAE RLNNMPLPPD
NC: TAINLLLKRV DEDIRRRQRF IADAAHELRT PMTALSLQAE RLNNMPLPPD

NM: AARQPAVLQQ SIRRNKHLLE QLLALARSQS DETPLTKTTF GLQSRFRQVL
GC: AGRQSAVLQQ SIRRNKHLLE QLLALARSQS DEPPLAKTTF GLQSRFRQVL
NC: AARQSAVLQQ SIRRNKHLLE QLLALARSQS DETPLTKTTF GLQSRFRRVL

NM: QELMPLALEK RQDIGVAVGG DVEVSADETE IYTLIKTFAD NAVRYTPPEG
GC: QELMPLVLEK RQDIGVAVGG DVEVSADETE IYTLVKTFAD NAVRYTPNGG
NC: QELMPLALEK RQDIGVAVEG DFEIFADETE IYTLVKTFVD NAIRYTPSEG

NM: RIDLGFTDEG KYLAVWVEDN GNGIPESERA RVLDPFYRIL GTEQQGTGLG
GC: RIDLGFTDEG KYLAVWVEDN GNGIPESECA RVLDPFYRIL GTEQQGAGLG
NC: RIDLGFTDEG KYLAVWVEDN GKGIPESER

NM: LSIADTLAKK YGGHLELTDS RRFGHGLLIR ALLDKETLK*
GC: LSIADTLAKK YGGYLELTDS RRFGHGLLIR ALLDKETLK*
```

TWO-COMPONENT SYSTEM THAT CONTROLS BACTERIAL MEMBRANE SYNTHESIS

CROSS-REFERENCE TO RELATED APPLICATIONS

This application is a continuation of U.S. patent application Ser. No. 09/439,226, filed Nov. 12, 1999 now U.S. Pat. No. 6,518,037, which is incorporated herein by reference.

STATEMENT OF GOVERNMENT RIGHTS

The United States government sponsored the research leading to this invention under grants AI18384 and AI43924 from the National Institutes of Health. The Government retains certain rights in this invention.

BACKGROUND OF THE INVENTION

*Neisseria gonorrhoeae* ("gonococcus") and *N. meningitidis* ("meningococcus") are Gram-negative diplococci that are strictly human pathogens. *N. gonorrhoeae* causes primarily urethritis in males and pelvic inflammatory disease in females. *N. meningitidis* is the causative agent of middle ear infections and meningitis.

As is commonly found in other bacterial pathogens, strains of *Neisseria* sp. vary greatly in pathogenicity. Treatment and outcome of neisserial infections are dictated by pathogenicity. For example, *N. meningitidis* is frequently found in the throat of normal humans, where it can reside as a commensal without causing symptoms. However, virulent strains of *N. meningitidis* may cause a fulminating meningitis, resulting in brain damage or death before treatment can control the disease. Diagnostic methods to date have not been useful in distinguishing the mild, commensal *Neisseria meningitidis* from the virulent strains.

The standard method of diagnosing a bacterial disease is culturing, followed by identification by immunoreactivity, morphology, and biochemical reactions. In the case of neisserial pathogens, because of its fastidious growth requirements, the organism has often lost viability and will no longer grow in culture once isolated from the patient. U.S. Pat. No. 4,446,230 discloses a test method and bacterial strain for the laboratory diagnosis of gonorrhea. This strain can be maintained in a laboratory and will become transformed by exogenous neisserial DNA, even from a non-viable clinical sample. The transformation corrects an induced specific growth requirement, thereby permitting the strain to grow. However, this test does not distinguish virulent from non-virulent strains.

In vivo models of *N. gonorrhoeae* infection using male human volunteers have been done to elucidate the factors that contribute to bacterial virulence. However, such studies are costly and limited in scope. Recent tissue culture models of gonococcal infection have begun to define the interactions between the bacterium and the host. In brief, it is evident that the bacteria attach and invade human urethral epithelial cells, a niche that probably represents the primary site of infection during the course of urethritis. Gonococci reside and replicate within vacuoles within these cells. Infected cells can rupture or be shed into the urethral lumen, releasing gonococci to invade neighboring epithelial cells or to be excreted in the urine. Several gonococcal components, including pili, Opa proteins and lipooligosaccharide (LOS) have been implicated in the ability of gonococcus to attach to and invade host cells, and implicated in the pathogenesis of gonococcal infection.

Our current knowledge clearly suggests that the gonococcus exists within different environments during the course of infection, such as extra- and intra-cellular and vacuolar locations. It is also likely that the site of infection of *N. gonorrhoeae*, the genital tract, differs significantly between males and females. How *N. gonorrhoeae* adapts to these different conditions is not well understood. It has been observed that a gonococcus thought to be pathogenic quickly converts to a less virulent type under the conditions of culture that are used to identify the bacterium and to test for antibiotic sensitivity.

Current treatment of neisserial infections is with broad spectrum antibiotics. However, treatment with broad spectrum antibiotics leads to the disturbance of the natural microflora, leaving the patient susceptible to infections with such opportunistic pathogens as *Candida albicans* and *Gardnerella*. An antibiotic targeted specifically at pathogenic, rather than commensal *Neisseria*, would avoid this complication. It is currently difficult to test virulent clinical isolates of *Neisseria* to determine each strain's sensitivity to targeted-specificity antibiotics because of the difficulty of maintaining virulence during growth of the strains in culture. Therefore, such an antimicrobial sensitivity test as is disclosed in U.S. Pat. No. 5,789,173 may not be useful in determining neisserial sensitivity to antibiotics.

If the factors that convert a commensal, mildly or non-pathogenic *Neisseria meningitidis* or *N. gonorrhoeae* into a pathogenic, invasive bacterium were known, it would be possible to use the identification of such factors as an aid for the diagnosis and therapy of neisserial disease. There is a need to determine these so that they can be used as a target in screening bacteriostatic or bacteriocidal drugs that are selectively effective against virulent *Neisseria*.

BRIEF SUMMARY OF THE INVENTION

The present invention provides a mutant *Neisseria* bacterium having excessive outer membrane. The bacterium may be *Neisseria gonorrhoeae* or *Neisseria meningitidis*.

The present invention also provides a method of identifying a pathogenic bacterium comprising culturing under identical conditions 1) a mutant *Neisseria* bacterium having excessive outer membrane, 2) a wild type *Neisseria* and 3) a clinical sample taken from a patient suspected of having a neisserial infection; examining the extent of blebbing in each cultured bacterium; and comparing the extent of blebbing of the clinical sample to that to the bacterium having excessive outer membrane and to that of the wild type *Neisseria* so as to determine the pathogenicity of the clinical sample.

The present invention further provides a method of identifying an inhibitor compound of virulent *Neisseria* providing a culture containing a bacterium having a mutation which results in blebbing of the outer membrane and the test inhibitor compound, and providing a culture containing a wild type bacterium having no blebbing and the test inhibitor; and comparing the growth of the mutant bacterium to that of the wild type in order to identify an inhibitor compound that inhibits the growth of the mutant to a greater degree than the inhibitor compound inhibits the growth of the wild type.

The present invention further provides individual, isolated proteins coded for or otherwise under the control of the two-component system, the presence of which quickly and easily determined and is indicative of virulence.

DESCRIPTION OF THE DRAWINGS

FIG. 2 shows the alignment of the amino acid sequences of the BmrR open reading frames (ORF) from *N. gonorrhoeae* (GC) (SEQ ID NO:2, SEQ ID NO:3), *N. meningitidis* (NM) (SEQ ID NO:1; SEQ ID NO:10; SEQ ID NO:11) and *N. cinerea* (NC) (SEQ ID NO:4); and the alignment of the amino acid sequences of the BmrS ORFs from GC (SEQ ID NO:6), NM (SEQ ID NO:5), and NC (SEQ ID NO:7)

DETAILED DESCRIPTION OF THE INVENTION

*Neisseria gonorrhoeae* and *N. meningitidis* are strictly human pathogens. Current knowledge of the pathogenesis of these organisms suggests that these bacteria encounter different environments within the host during infection. However, little is known of how *Neisseria* sense and respond to these different environments or what systems contribute to virulence. Many bacteria respond to changes in their environment through changes in the expression level of particular genes. Two-component regulatory systems are now recognized as significant mediators of signaling in bacteria, relaying environmental signals that produce changes in gene expression patterns. During signal transduction by a typical two-component regulator, a membrane sensor protein detects a specific environmental stimulus presumably either through a direct interaction with a ligand or through conformational changes induced by changes in environmental conditions. Such a regulatory system might be useful as a diagnostic marker of virulence in *Neisseria*.

However, information regarding signaling within the gonococcus is limited. Previously a two-component regulator-like system was reported in pilus gene expression, although the environmental cue to which the system responds is unknown. Since membrane blebbing has been found to be associated with virulence, it was thought that a quantitative assay of the amount of membrane would be indicative of increased virulence. In order to further investigate a possible two-component regulator-mediated signaling pathway in *N. gonorrhoeae*, the polymerase chain reaction (PCR) with degenerate oligonucleotide primers was used to amplify a region from the DNA-binding component of a novel *N. gonorrhoeae* two-component regulator.

This regulatory system is known to be present in other *Neisseria* species and to have a role in outer-membrane blebbing. The term "blebbing" is used to mean the bubble- or blister-like extrusion of membrane from the surface of the bacterial cell. The term "high-blebbing" is used to describe bacteria showing such extensive outer membrane formation. "Blebs" are easily separated from the outer membrane by mild physical manipulation, such as differential centrifugation.

Outer membrane bleb formation by *Neisseria meningitidis* and *N. gonorrhoeae* has long been recognized as an important factor in *Neisseria* infection, particularly that due to *N. meningitidis*. Numerous membrane blebs were found at the tissue surface during ultrastructural analysis of cervical gonorrhoea (Evans et al. J. Infect. Dis. (1977) 136:248–255) and a meningococcus recovered from the plasma of an infected patient contained multiple, long membranous protrusions typical of blebbing (Brandtzaes et al. J. Infec. Dis. (1989) 155:195–204). Lipooligosaccharide (LOS), which is a component of the blebs shed by the gonococcus and meningococcus, has major physiological effects during sepsis and meningitis caused by *N. meningitidis* and the plasma LOS levels are closely correlated to prognosis. Furthermore, compartmentalization of LOS production correlates with the clinical presentation in meningococcal infection. LOS levels in patients defined as having septicaemia showed high levels in plasma (median 3500 ng/ml) and low levels in cerebral spinal fluid, while with patients with meningitis, LOS was detectable in the plasma of three out of 19 patients and in the CSF in 18 of 19 patients, with median levels of 2500 ng/ml.

From these observations, it is possible that blebbing is both the indicium and the cause of pathogenicity in *Neisseria*. Agents that control or inhibit blebbing may be useful in therapy against *Neisseria* infections. However, the standard laboratory cultures of *Neisseria* typically show little or no blebbing after repeated laboratory passage and are therefore not useful in screening for agents that control or inhibit blebbing. Identification of the degree of blebbing of newly isolated strains from clinical samples may be an early indication of the virulence of the pathogen and whether immediate, aggressive therapy is necessary.

Factors affecting the blebbing process are poorly understood. Strains of meningococcal serogroup A, B and C release membrane blebs in the log phase of growth but not in the lag phase, suggesting some form of regulation. The identification of a putative regulatory system, the mutation of which produces clear differences in the blebbing process is potentially of great interest to improvement of therapeutic strategies for treatment of *Neisseria* infections in which blebbing is a serious complication.

During the course of investigation, mutation of the genes controlling blebbing was successful, and after insertion into a strain, the resultant high-blebbing bacterium is a "super blebber" that shows extensive membrane blebbing in all culture conditions. Unlike virulent, high-blebbing clinical isolates of *Neisseria*, these super blebber mutants, termed bmrRS, are stable and do not revert to non-blebbing strains on repeated culture. For this reason, they are particularly useful as controls to estimate the virulence of clinical samples, for the production of neisserial membranes for use as a vaccine and for screening of antibiotics targeted at virulent *Neisseria*.

Outer membrane proteins and LOS are known to be useful as vaccines. (See, e.g., U.S. Pat. No. 5,902,586 issued May 11, 1999 to Jennings et al.) Because the super blebbers produce two to four times as much outer membrane as do wild type strains, they are a particularly useful source of neisseria vaccine material. Thus, a novel two-component regulatory system has been identified in *N. gonorrhoeae, N. meningitidis* and *N. cinerea*. DNA sequence analysis suggested that the system may be non-functional in laboratory strains of *Neisseria*. However, experimental mutation of the system in each of the three species resulted in increased membrane production in the mutant compared to the wild type. This correlated with an increase in outer membrane blebbing. These data suggest that outer membrane blebbing, which is regarded as an important contributor to the pathogenesis of neisserial diseases, is regulated as part of a coordinated response to environmental cues.

The references identified in the specification are incorporated herein by reference to the extent that they supplement, explain, provide a background for or teach methodology, techniques, and/or compositions employed herein.

The following examples are included to demonstrate the preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the concept and scope of the invention. More specifically, it will be apparent that certain agents, such as DNA constructs, that are both chemically and biologically equivalent may be substituted for the agents described herein while the same or equivalent results would be achieved. It will also be apparent that the techniques are not limited by the order in which the steps are carried out. All such substitutions and modifications apparent to those skilled in the art are deemed to be within the spirit and scope of the invention as defined by the appended claims.

The present invention provides a target for control of the neisserial membrane synthesis. The present invention also provides a quantitative assay of neisserial membrane. The present invention also provides a neisserial bacterium with increased amounts of membrane, more specifically, blebs of outer membrane, which bacterium is useful as a production cell for isolation of vaccine related membrane proteins and glycolipids. The present inventions also provides a standard with which to compare clinical isolates of *Neisseria* spp. in order to estimate the pathogenicity of such isolates. The present invention also provides a screening assay for drugs that are specifically effective against virulent strains of *Neisseria*.

The invention is illustrated by the following examples.

EXAMPLE 1

Construction of the Super Blebber

A. Bacterial Strains and Plasmids

Wild type *Neisseria* strains used were *N. gonorrhoeae* 1291, *N. meningitidis* NMB and *N. cinerea* 601. *Neisseria* were grown on solid GC Base medium (Difco Laboratories, Detroit) supplemented with amino acids and vitamins. For growth of kantamycin resistant *Neisseria*, BHI agar was used (Difco) supplemented with 2.5% FCS. Liquid *Neisseria* cultures were grown in proteose peptone broth (proteose peptone No. 3, Difco) 15 grams per liter; soluble starch (Difco) 1 gram per liter, dibasic potassium phosphate 4 grams per liter; monobasic potassium phosphate 1 gram per liter; sodium chloride 15 grams per liter or in Morse's defined medium.

*Escherichia coli* strain XL1-Blue (Stratagene, LaJolla, Calif.) was used to maintain plasmids and was grown in liquid culture using LB broth or on solid medium using LB agar. Antibiotics were used at the following concentrations: ampicillin 100 µg/ml; kanamycin 50 µg/ml (*E. coli*) or 25 µg/ml (*Neisseria*), erythromycin 150 µg/ml (*E. coli*) or 1 µg/ml (*Neisseria*).

pBluescript (Stratagene), pUC18 (Pharmacia, Piscataway, N.J.) and pCRII.I (Invitrogen, Carlsbad, Calif.) were used as cloning vectors. PUC4K (Pharmacia) was used as a source of kanamycin cassette. Erythromycin resistance cassette was derived from pKErmC' plasmids (Zhou, D. G. and M. A. Apicella (1996) Gene 171:133–134.)

Plasmid DNA was prepared using Qiagen plasmid DNA preparation (Qiagen Inc., Chatsworth, Calif.). Chromosomal DNA was prepared from plate grown bacteria which were scraped from the plate into 100 µl of phosphate buffered saline (PBS). Cells were then pelleted by spinning for one minute at top speed in a microfuge before resuspension in 250 µl of TNE (10 mM Tris-HCl pH 8, 100 mM NaCl, 1 mM EDTA.) 25 1 of 10% SDS were added followed by 25 µl of Proteinase K (25 mg/ml). The reaction was incubated overnight at 55° C. and then extracted twice with phenol and then twice with phenol/chloroform. DNA was precipitated by addition of 10 µl 3M sodium acetate pH 5.4 and 1 ml 100% ethanol, lifted from the tube on the end of a pipette tip and washed by repeated transfer to tubes containing 500 µl 70% ethanol. Washed DNA samples were air dried before resuspension in 100 µl TE RNase.

DNA sequencing was performed at the University of Iowa DNA sequencing facility using dye terminator sequencing chemistry with AmpliTaq DNA polymerase, FS enzyme (PE Applied Biosystems, Foster City, Calif.). The reactions were run on and analyzed using an Applied Biosystems Model 373A stretch fluorescent automated sequencer.

PCR was performed using Boehringer Mannheim (Philadelphia) reagents according to the protocols provided. PCR-DOP was performed using degenerate oligonucleotides as described by Wren et al (FEMS Microbial Letters (1992) 99:287–291). PCR products were directly cloned using the TA cloning system (Invitrogen) according to the manufacturer's instructions.

B. Results of PCR Amplification and Cloning in *N. gonorrhoeae*

PCR using the degenerate oligonucleotides described by Wren produced a product of the expected size (322 bp) from a *N. gonorrhoeae* genomic DNA template. The product was cloned and numerous clones were analyzed through DNA sequencing. This revealed that the PCR product contained many different DNA fragments that were clearly not from two-component regulator genes, which is in contrast to the report in which the same primer sequences amplified a region of two-component systems from numerous other bacteria without this apparent non-specific effect.

A single clone of 322 bp was obtained which through analysis of its deduced amino-acid sequence clearly contained the 5' region of the DNA-binding component of a two-component regulatory system. This clone was not identical to the pilAB system of *N. gonorrhoeae*.

Using the 322 bp PCR product as a probe, several genomic libraries were screened, but no positive signals were observed, although a Southern blot of *N. gonorrhoeae* genomic DNA identified several restriction fragments to which the probe stringently hybridized. Attempts to clone these fragments, all of which were 4 kbp or greater in size, failed. These fragments, which might have contained the entire two-component system sought, could not be cloned, suggesting that the system was toxic to *E. coli* when carried at high copy number. However, two Sau3AI fragments which were identified by the Southern analysis were successfully cloned and found to contain open reading frames (ORFs) that encoded for the majority of a two-component regulator, based on their deduced amino acid sequence. Successive cloning of other small genomic fragments, containing small parts of the two-component regulator, followed by reconstruction, produced a sequence contig of 3.97 kbp. that contained the two ORFs of the putative two-component regulator and partial ORFs upstream and downstream of the system. We have named this two-component system bmr (for bacterial membrane regulator, see below). The upstream ORF was homologous to a hypothetical membrane protein of *Bacillus subtilis* (Genbank submission number P42308) and the downstream ORF was homologous to the cytoplasmic axial filament protein CafA, of *E. coli* (FIG. 1.) *N. gonorrhoeae* bmrRS has been deposited with the American Type Culture Collection (P.O. Box 1549, Manassas, Va., 20108) under the accession number PTA-801.

Comparison of the deduced amino acid sequence of the putative two-component regulator to the amino acid sequences of the Genbank database revealed homology to numerous other two-component regulators. The highest degree of homology was to the BasRS system of *E. coli* and *Salmonella typhimurium* and the putative Bas homologue in *Haemophilus influenzae*. The Bas system of *E. coli* and *S. typhimurium* is involved in regulation of lipopolysaccharide (LPS) substitution by phosphate and aminoarabinose, that in the case of *S. typhimurium* is implicated in LPS changes during the course of infection. This degree of homology is frequently found in bacteria. Biochemical capabilities of the bacteria are modified and extended by the duplication and subsequent mutation of genes, resulting in gene products with considerable degrees of homology, but having different functions and characteristics, as is seen in the bas and bmr gene products.

An interesting feature of *N. gonorrhoeae* bmr was the presence of a stop-codon at the fourteenth codon position of the DNA-binding component that was predicted to terminate translation of this ORF at that Point (FIG. 2.)

C. Cloning of bmr From Other *Neisseria*

Figure 1:
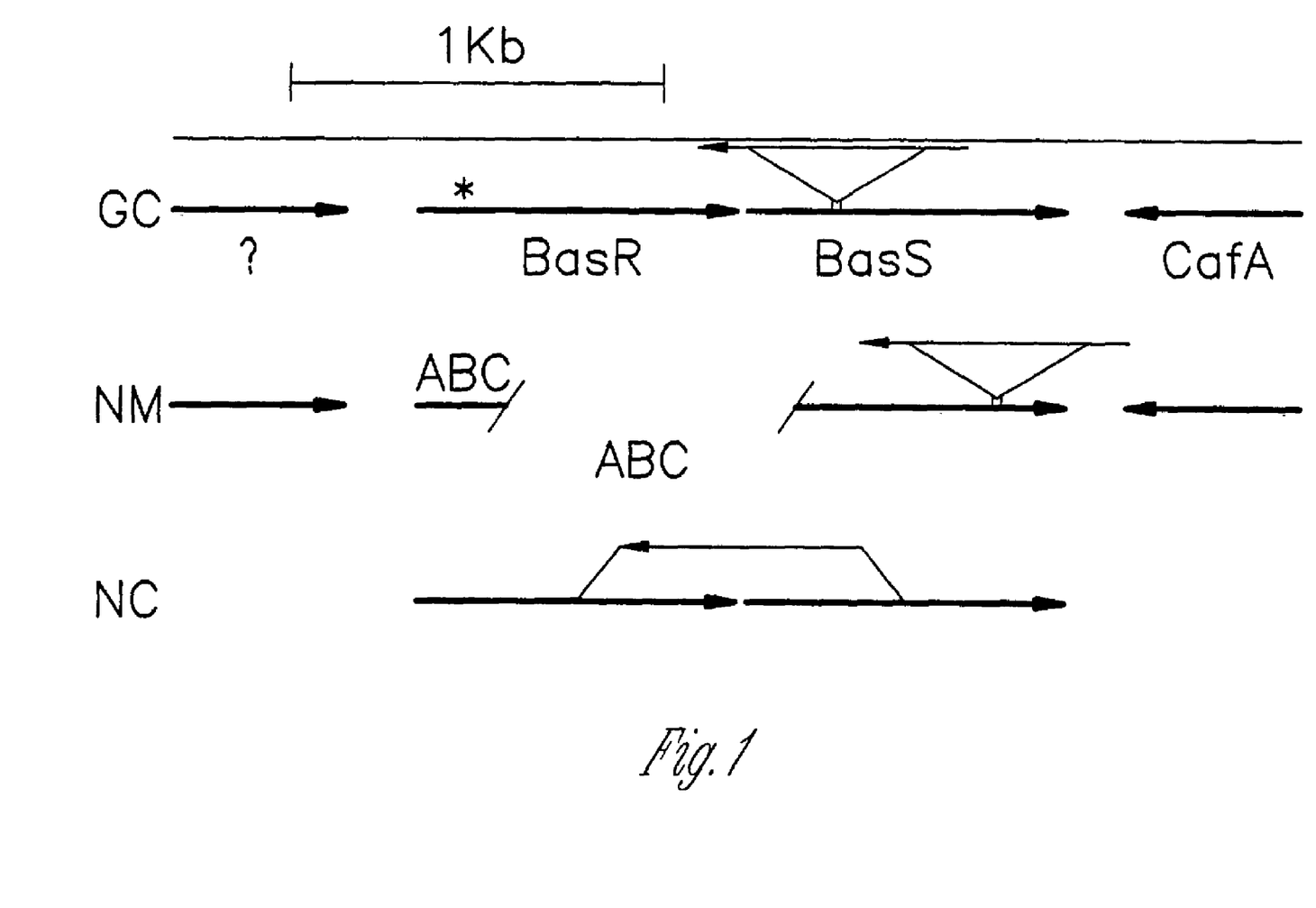
FIG. 1 shows a diagram of the bmr locus of *N. gonorrhoeae* (GC), *N. meningitidis* (NM) and *N. cinerea* (NC).

*N. meningitidis* is closely related to *N. gonorrhoeae* and *N. cinerea* is a non-pathogenic member of the *Neisseria* genus. Southern blots of genomic DNA from these two bacteria, using the *N. gonorrhoeae* 322 bp PCR product as a probe, identified stringently hybridizing restriction fragments in each of these organisms. Using a strategy similar to that described above, the bmr locus was cloned from *N. meningitidis* and *N. cinerea*. The predicted amino acid sequences of the three loci are highly homologous, strongly suggesting that the equivalent locus from the three species had been cloned (FIG. 2). However, in *N. meningitidis*, a T to G substitution altered the premature TAA stop-codon of *N. gonorrhoeae* to a GAA glutamate codon. In *N. cinerea*, the codon was also for glutamate, but read GAG. However, the *N. meningitidis* locus contains a 591 bp deletion compared to both *N. gonorrhoeae* and *N. cinerea* that results in deletion of the 3' 486 bp of the putative DNA-binding component-encoding ORF, the intergenic region and the 5' 69 bp of the putative sensor-encoding ORF (FIG. 1.) In addition, other nucleotide differences in the *N. meningitidis* locus immediately preceding the deletion cause frame shifts of the BmrR ORF (FIG. 2.) Thus, *N. meningitidis* is not predicted to encode a BmrR protein. Although the 5' 23 codons of the sensor-encoding ORF are deleted, an alternative initiation codon may allow translation of a near-full length sensor protein in *N. meningitidis*. The bmr locus was amplified by PCR from numerous *N. meningitidis* strains, including several from serotypes A, C and W 135. The primers used (5' CCTGTCCGTGTGTTGCAATC 3' (SEQ ID NO:8) and 5' CCGTTCCCGTTATCCTCCAC 3') (SEQ ID NO:9)) amplify the region starting 166 bp upstream of the initiating codon of the deleted BmrR ORF and ending 200 bp upstream of the termination codon of the putative BmrS ORF. All of these PCR reactions produced a band of the same size as that from strain NMB (i.e., approximately 600 bp smaller than the fragment amplified from *N. gonorrhoeae*) (data not shown) suggesting that the deletion in bmr is common to many, if not all, *N. meningitidis* strains. *N. meningitidis* bmrRS has been deposited with the American Type Culture Collection (P.O. Box 1549, Manassas, Va., 20108) under accession number PTA-800.

An *N. gonorrhoeae* bmrS insertion mutant was constructed by insertion of an erthromycin resistance cassette at the site indicated in FIG. 1. An insertion mutant of *N. meningitidis* was constructed by insertion of a kanamycin resistance cassette within the sensor coding region (FIG. 1.) The locus was mutated in *N. cinerea* by deletion of an internal BsrGI fragment and insertion of a kanamycin resistance cassette in its place. This mutation deletes the 3' 418 bp of bmrR and the 5' 565 bp of bmrS (FIG. 1).

FIG. 2 shows the alignment of the amino acid sequences of the BmrR and BmrS ORFs from the three *Neisseria* spp. The GC BmrR ORF contains a stop codon (*) at the fourteenth codon. The NM BmrR sequence contains a small deletion compared to the GC and NC sequences after the $34^{th}$ codon, resulting in a frameshift (denoted by the amino acid sequence written on the line above). The amino acid sequences in frame with the N-terminal NM BmrR ORF is closed by the presence of a stop codon (*). Following the frameshift, a small insertion results in the presence of the amino acids FVPLA (SEQ ID NO:12) in the NM sequence that is absent from both GC and NC. Following this is a large deletion that removes the remainder of the BmrR ORF and the N-terminal 23 codons of the BmrS ORF. Outside of this region, the three sequences are highly homologous.

EXAMPLE 2

Characteristics of the Super Blebbers

A. Chemical Analysis of the Outer Membrane of the Super Blebbers

The effect of the bmr mutation on several parameters was investigated by comparison of the *N. gonorrhoeae* wild-type and the mutant. Overnight cultures (10 ml) were killed by the addition of 0.5% phenol for two hours and outer membrane enriched samples were isolated as described by Zollinger et al., International Symposium, Hanasaari, Espoo, Finland (1991). Samples were analyzed by SDS-PAGE on a 6–15% gradient gel. LOS was isolated by phenol/chloroform/petroleum ether extraction as described by Galanos et al. Eur. J. Biochem.(1969) 9:45–249 and analyzed as described by Lee et al. J. Biol. Chem. (1995) 270:271151–9. The growth rate and outer membrane protein profile of the mutant were unaltered from the wild type.

Because of the homology of the *Neisseria* locus to the previously characterized bas locus of *E. coli* and *S. typhimurium* and the involvement of this system in LPS modulation in those bacteria, LOS was isolated from wild type and mutant and analyzed by mass spectrometry. No difference was found, showing that despite the homology, the system functioned differently in *Neisseria* and those other bacteria.

B. Morphology of the Super Blebbers

For scanning electron microscopy (SEM), samples of proteose peptone broth cultures were taken directly without centrifugation or washing. Processing included treatment with 1% osmium tetroxide prior to dehydration through a graded ethanol series, with a final clearance in hexamethyldisilane (HMDS from Polysciences, Inc. Warrington, Pa.). After coating with gold-palladium, the specimens were viewed on an S-4000 Hitachi scanning electron microscope at 5 kV accelerating voltage.

For transmission electron microscopy, the samples were dehydrated in a graded ethanol series prior to embedment in LR White resin (Ted Pella, Inc., Redding, Calif.) and sectioned to approximately 85 nm thickness using an ultramicrotome. Samples were counter-stained with 5% uranyl acetate for viewing with an H-7000 Hitachi transmission electron microscope at 75 kV accelerating voltage.

Figure 3:
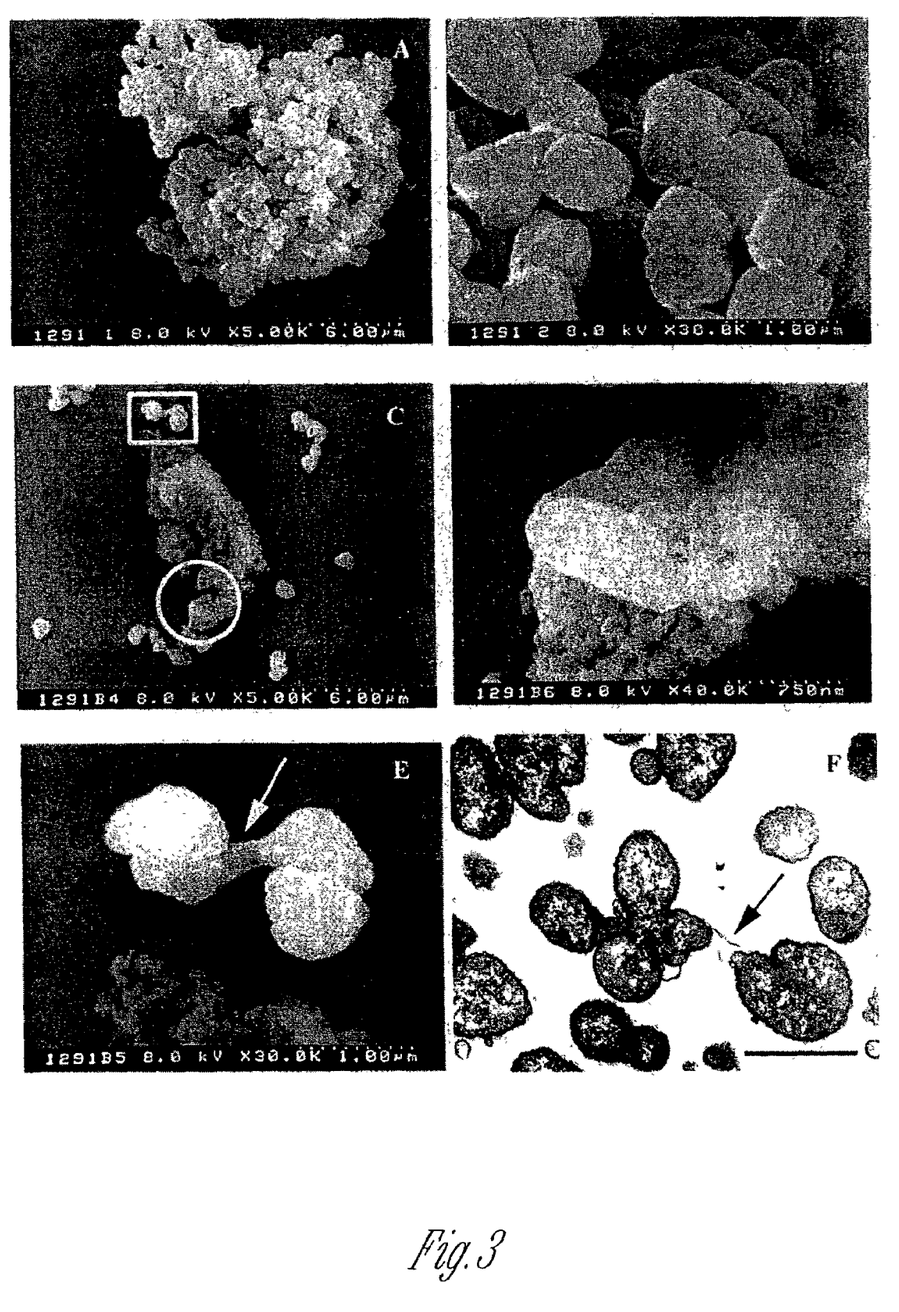
FIG. 3 shows scanning electron micrographs of wild type and mutant *N. gonorrhoeae*.

SEM analysis revealed that the wild type and mutant bacteria differed in two ways. Wild type *N. gonorrhoeae* were observed to be distinct diplococci with a smooth appearance. (FIGS. 3A and 3B) However, the mutant produced large numbers of blebs. (FIGS. 3C and 3D) Shedding of outer-membrane particles (blebbing) is a characteristic of *Neisseria*. In these analyses the mutant bacteria were blebbing to a much higher degree than the wild type. In addition, many mutant diplococci were joined to others by membranous connections (FIGS. 3C and 3E). When viewed by TEM, the connections did not contain electron dense material of the cytoplasm, suggesting that they consist of hollow membrane tubes joining pairs of diplococci. (FIG. 3F). These connections were not observed with the wild type.

Figure 4:
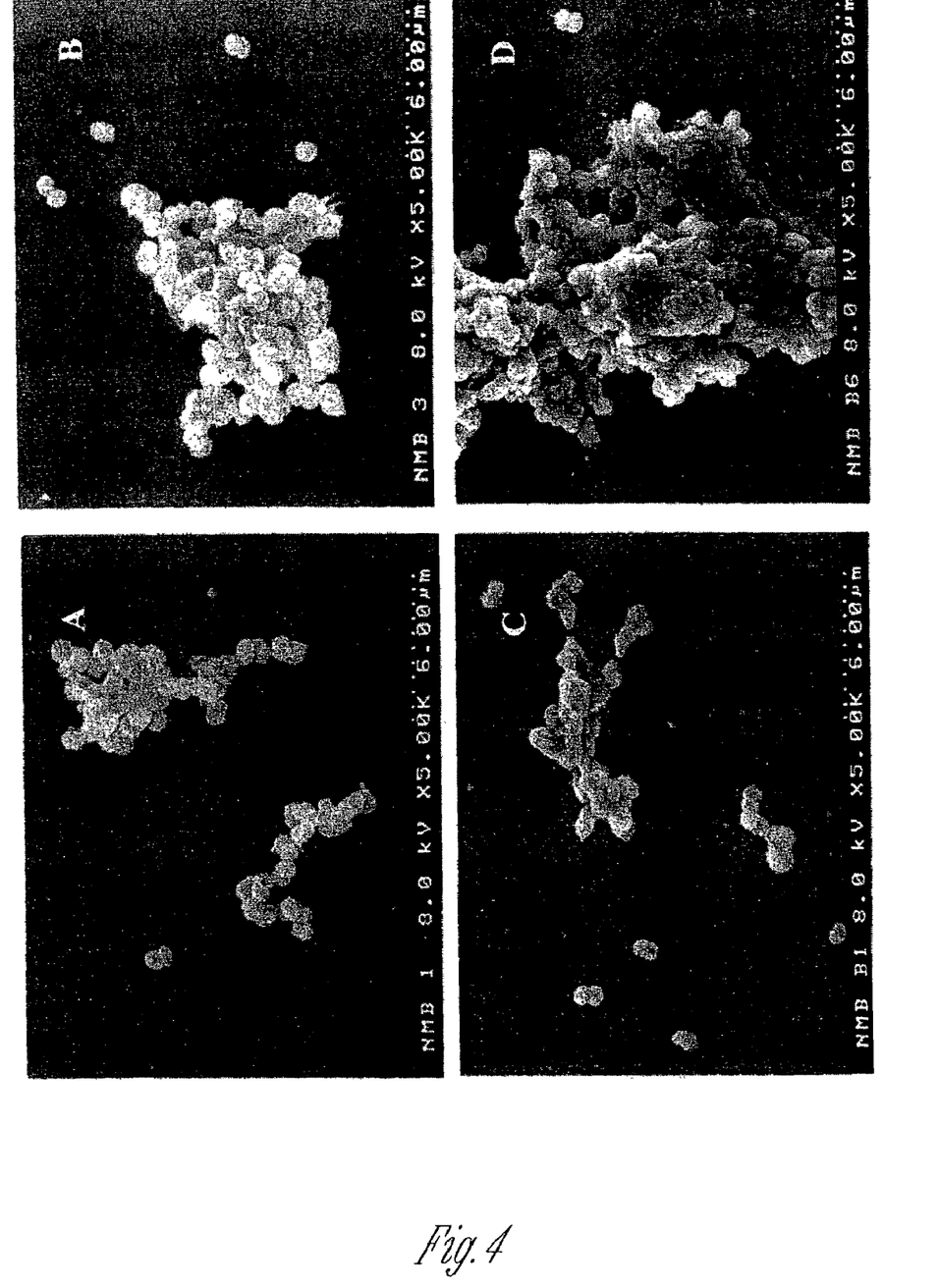
FIG. 4 shows scanning electromicrographs of wild type and mutant *N. meningitidis*.

The morphological changes seen in the *N. meningitidis* bmr mutant are shown in FIGS 4A and 4B. As observed with the mutant *N. gonorrhoeae*, these mutants were also joined by membranous connections. The bmr mutant of *N. cinerea* showed similar changes in morphology.

C. Phospholipid Analysis

The electron micrographs suggested that the mutants had alterations in their membranes that resulted in an increase in membrane material. To test this hypothesis, wild type and mutant *N. gonorrhoeae* were grown in the presence of $^{14}C$-labeled acetate to label phospholipid and allow quantitation of membrane produced by the bacteria.

Bacteria were grown in 5 ml of Morse's defined medium supplemented with 4 μCi/ml $^{14}C$-labeled acetate. *N. meningitidis* was grown for 5 hours and *N. gonorrhoeae* was grown for 20 hours at 37° C. in a shaking incubator to achieve the appropriate bacterial growth. For *N. gonorrhoeae*, the blebs were separated from the bacteria by underlaying the cultures with 2.5 ml of 10% sucrose in balanced salt buffer in centrifuge tubes and centrifuging in a SW-40 Ti rotor (Beckman, Palo Alto, Calif.) at 10,000 rpm at 4° C. for 30 minutes. The supernatant above the sucrose cushion was transferred to fresh centrifuge tubes. The sucrose cushion was removed for scintillation counting. The supernatant was centrifuged in a SW-40 Ti rotor at 25,000 rpm (100,000×g) for 75 minutes at 4° C. to pellet blebs. The supernatant from this spin was removed for scintillation counting. The centrifuge tube was partially dried using cotton swabs.

Labeled phospholipids were isolated by extraction with 100 μl of chloroform and 200 μl of methanol added to the sample and vortexed for 2 minutes. A further 100 μl of chloroform was added followed by 30 seconds of vortexing. 100 μl of deionized water was added followed by 30 seconds of vortexing. The mixture was centrifuged at 13,000 rpm in a microfuge for ten minutes at room temperature. The upper layer was removed for scintillation counting. The lower layer was removed from below the interface pellet and centrifuged before scintillation counting.

Blebs were separated from whole cells and the phospholipids in both samples extracted. The counts present in both bleb and cell-associated phospholipids are presented in Table I.

TABLE I $^{14}C$-acetate Incorporation, Counts per Minute
*N. gonorrhoeae* strain 1291, wild type and bmr mutant

|  | Experiment 1 | Experiment 2 | Experiment 3 |
|---|---|---|---|
| Wild Type |  |  |  |
| Total CPM | $7.4 \times 10^7$ | $5.7 \times 10^7$ | $7.1 \times 10^7$ |
| CPM in cell-associated phospholipids | $5.7 \times 10^6$ | $4 \times 10^6$ | $4.8 \times 10^6$ |
| CPM in bleb-associated phospholipids | $2.5 \times 10^4$ | $8.1 \times 10^4$ | $5 \times 10^4$ |
| Mutant |  |  |  |
| Total CPM | $6.8 \times 10^7$ | $6.7 \times 10^7$ | $6.8 \times 10^7$ |
| CPM in cell-associated phospholipids | $7.3 \times 10^6$ | $4.8 \times 10^6$ | $5.6 \times 10^6$ |
| CPM in bleb-associated phospholipids | $5.2 \times 10^4$ | $3.1 \times 10^5$ | $2.1 \times 10^5$ |
| Ratio of mutant to wild type cell-associated CPM | 1.3 | 1.2 | 1.2 |
| Ratio of mutant to wild type bleb-associated CPM | 2.1 | 3.8 | 4.2 |

In each of these three experiments, *N. gonorrhoeae* 1291 bmr incorporated increased amounts of label compared to wild type. Both cell-associated and bleb-associated label was increased in the mutants. The increase in cell-associated counts was slight, which agrees with microscopy observations in which the mutant and wild type bacteria did not appear different except for the presence of connections between mutant diplococci and increased level of blebbing in the mutant. As would be expected from the morphology, mutant bleb-associated counts were between two- and four-fold higher than wild type.

Labeling experiments were also conducted using *N. meningitidis*. For unknown reasons, it proved difficult to obtain consistent bleb-associated counts with these bacteria. The micrographs suggested that the membrane alteration observed with these mutants did not involve the type of blebbing seen in the gonococcus, but instead involved cell-associated membrane changes. However, total membrane was increased as was seen in the *N. gonorrhoeae* experiments. Table II shows a comparison of total outer membrane counts from both wild type and mutant bacteria. Increased incorporation of counts in the mutants was observed.

TABLE II $^{14}C$-acetate Incorporation, Counts per Minute
Wild type and bmr mutant of *N. meningitidis* NMB

|  | Experiment 1 | Experiment 2 |
|---|---|---|
| Wild-Type |  |  |
| Total CPM | $4.0 \times 10^8$ | $6.0 \times 10^7$ |
| Total phospholipids | $1.0 \times 10^7$ | $5.4 \times 10^6$ |
| Mutant |  |  |
| Total CPM | $4.0 \times 10^8$ | $6.0 \times 10^7$ |
| Total phospholipids | $1.9 \times 10^7$ | $9.7 \times 10^6$ |
| Ratio of mutant to wild-type CPM | 1.9 | 1.8 |

When larger quantities of membrane are desired, the culturing and purification may be easily scaled up.

EXAMPLE 3

Use of the *Neisseria* bmr Mutants to Estimate Virulence of Bacteria Recovered from Clinical Samples Swabs from suspected *Neisseria* infections are cultured for meningococcus or gonococcus by the methods disclosed in Example 1. A laboratory strain of *Neisseria* and a super blebber are grown in the same manner as controls. Overnight cultures are examined for blebbing in the SEM as described in Example 2B.

Phospholipids are isolated as described in Example 1. Phospholipids are quantitated as described by the incorporation of radionuclide or by HPLC analysis of total phospholipids. A level of phospholipid close to that of the super blebber indicates infection with a virulent neisserial pathogen, indicating that therapy should be immediate and aggressive.

As seen in Table III, a quantitative estimate on a scale of 1 (no blebbing) to 3 (many blebs and filamentous connections between cells) and the phospholipid content that correlates with blebbing are made to determine virulence of the clinical sample.

TABLE III

| | Blebbing | Phospholipid CPM* | Diagnosis |
|---|---|---|---|
| *N. gonorrhoeae* strain 1291 | 1 | $6 \times 10^4$ | |
| Super blebber | 3 | $2 \times 10^5$ | |
| Hypothetical Sample #1 | 1 | $6 \times 10^4$ | Not virulent, therapy not needed |
| Hypothetical Sample #2 | 2 | $1 \times 10^5$ | Moderate virulence, therapy indicated |
| Hypothetical Sample #3 | 3 | $>1.8 \times 10^5$ | Highly virulent, immediate and aggressive therapy indicated |

*Phospholipid content is expressed as counts per minute $^{14}$C-acetate incorporation into phospholipid fraction.

EXAMPLE 4

Use of Super Blebbers to Screen Biocidal or Biostatic Agents

A ninety-six well culture is set up with *N. gonorrhoeae* Strain 1291 and the *N. gonorrhoeae* super blebber, and the *N. meningitidis* strain NMB and the *N. meningitidis* super blebber. Dilutions of the potentially selective antibiotics are added to respective wells. An antibiotic is considered selective if it inhibits the mutant organisms that show excessive blebbing as indicated by no growth in the super blebber chambers at lower concentrations than those that inhibit growth in the strains 1291 and/or NMB.

An compound may affect a specific property of the bacterium without outright killing of the organism. Such a compound may be particularly useful in that it does not disturb the normal microflora of a patient while inhibiting the specific property that renders a pathogen virulent. It would be particularly useful to identify a compound that targets the *Neisseria* blebbing process. A ninety-six well culture is set up with a recently isolated, high-blebbing *Neisseria* that shows excessive outer membrane formation as indicated by blebbing. Dilutions of the potentially selective antibiotics are added to respective wells. An antibiotic is considered selective if it inhibits the blebbing at lower concentrations that those that inhibit growth. Such an antibiotic may be considered to have converted the high-blebbing, virulent bacterium to a non-virulent form.

All of the compositions and methods disclosed and claimed herein can be made and executed without undue experimentation in light of the previous disclosure. While the compositions and methods of this invention have been described in terms of preferred embodiments, it will be readily appreciated by those of skill in the art that many variations and modifications may be applied to the compositions and methods and used in the steps or in the sequence of steps of the methods described herein without departing from the concept and scope of the invention. More specifically, it will be apparent that certain agents, such as vectors, primers and bacterial strains, that are both chemically and physiologically equivalent may be substituted for the agents described herein while the same or similar results would be achieved. All such similar variations and modifications apparent to those of skill in the art are deemed to be within the scope and concept of the invention defined by the appended claims.

All cited publications, patents, and patent applications are incorporated by reference herein, as though individually incorporated by reference.

We claim:

1. A cell comprising DNA encoding a *Neisseria* BmrR open reading frame (ORF) and DNA encoding a *Neisseria* BmrS ORF, wherein the BmrR ORF or the BmrS ORF contains an insertion or a deletion as compared to corresponding wild-type BmrR or BmrS ORF.

2. The cell of claim 1, wherein the BmrS ORF encodes a polypeptide having SEQ ID NO:5, SEQ ID NO:6, or SEQ ID NO:7.

3. The cell of claim 1, wherein the BmrR ORF encodes a polypeptide having SEQ ID NO:1, SEQ ID NO:2, SEQ ID NO:3, SEQ ID NO:4, SEQ ID NO:10 or SEQ ID NO:11.

4. The cell of claim 1, wherein the BmrS ORF encodes a polypeptide having SEQ ID NO:5, SEQ ID NO:6, or SEQ ID NO:7; and wherein the BmrR ORF encodes a polypeptide having SEQ ID NO:1, SEQ ID NO:2, SEQ ID NO:3, SEQ ID NO:4, SEQ ID NO:10 or SEQ ID NO:11.

5. The cell of claim 4, wherein the BmrS polypeptide is SEQ ID NO:5 and the BmrR polypeptide is SEQ ID NO:1, SEQ ID NO:10 or SEQ ID NO:11.

6. The cell of claim 5, wherein the BmrS polypeptide is SEQ ID NO:5 and the BmrR polypeptide is SEQ ID NO:1.

7. The cell of claim 5, wherein the BmrS polypeptide is SEQ ID NO:5 and the BmrR polypeptide is SEQ ID NO:10.

8. The cell of claim 5, wherein the BmrS polypeptide is SEQ ID NO:5 and the BmrR polypeptide is SEQ ID NO:11.

9. The cell of claim 4, wherein the BmrS polypeptide is SEQ ID NO:6 and the BmrR polypeptide is SEQ ID NO:2 or SEQ ID NO:3.

10. The cell of claim 9, wherein the BmrS polypeptide is SEQ ID NO:6 and the BmrR polypeptide is SEQ ID NO:2.

11. The cell of claim 9, wherein the BmrS polypeptide is SEQ ID NO:6 and the BmrR polypeptide is SEQ ID NO:3.

12. The cell of claim 4, wherein the BmrS polypeptide is SEQ ID NO:6 and the BmrR polypeptide comprises SEQ ID NO:2 and SEQ ID NO:3.

13. The cell of claim 4, wherein the BmrS polypeptide is SEQ ID NO:7 and the BmrR polypeptide is SEQ ID NO:4.

14. An isolated polynucleotide comprising:
   x(a) a BmrR ORF, wherein the Bmr ORF encodes a polypeptide comprising SEQ ID NO:1, SEQ ID NO:2, SEQ ID NO:3, SEQ ID NO:4, SEQ ID NO:10 or SEQ ID NO:11; or
   x(b) a BmrS ORF, wherein the BmrS ORF encodes a polypeptide comprising SEQ ID NO:5, SEQ ID NO:6, or SEQ ID NO:7.

15. An isolated polynucleotide construct comprising
   x(a) a BmrR ORF, wherein the Bmr ORF encodes a first polypeptide comprising SEQ ID NO:1, SEQ ID NO:2, SEQ ID NO:3, SEQ ID NO:4, SEQ ID NO:10 or SEQ ID NO:11; and
   x(b) a BmrS ORF, wherein the BmrS ORF encodes a second polypeptide comprising SEQ ID NO:5, SEQ ID NO:6, or SEQ ID NO:7, wherein the first polypeptide and the second polypeptide control *Neisseria* membrane synthesis.

16. The construct of claim 15, wherein the *Neisseria* is *Neisseria gonorrhoeae*.

17. The construct of claim 15, wherein the *Neisseria* is *Neisseria meningitidis*.

18. The construct of claim 15, wherein the *Neisseria* is *Neisseria cinerea*.

19. An isolated polynucleotide construct comprising DNA encoding a *Neisseria* BmrR open reading frame (ORF) or DNA encoding a *Neisseria* BmrS ORF, wherein the BmrR ORF or the BmrS ORF contains an insertion or a deletion as compared to corresponding wild-type BmrR or BmrS ORF.

20. An isolated polynucleotide construct comprising DNA encoding a *Neisseria* BmrR open reading frame (ORF) and DNA encoding a *Neisseria* BmrS ORF, wherein the BmrR ORF or the BmrS ORF contains an insertion or a deletion as compared to corresponding wild-type BmrR or BmrS ORF.

* * * * *

UNITED STATES PATENT AND TRADEMARK OFFICE
CERTIFICATE OF CORRECTION

PATENT NO. : 7,189,554 B2 Page 1 of 1
APPLICATION NO. : 10/288986
DATED : March 13, 2007
INVENTOR(S) : Michael A. Apicella and Andrew Preston It is certified that error appears in the above-identified patent and that said Letters Patent is hereby corrected as shown below:

On the cover sheet, field 57, "bmrRS" should be italicized, both times.

In column 25, line 11, claim 14, delete "x" before "(a)".

In column 25, line 15, claim 14, delete "x" before "(b)".

In column 25, line 19, claim 14, delete "x" before "(a)".

In column 25, line 23, claim 14, delete "x" before "(b)".

Signed and Sealed this

Sixteenth Day of October, 2007

JON W. DUDAS
*Director of the United States Patent and Trademark Office*

SEQUENCE LISTING

<160> NUMBER OF SEQ ID NOS: 12

<210> SEQ ID NO 1
<211> LENGTH: 73
<212> TYPE: PRT
<213> ORGANISM: Neisseria meningitidis

<400> SEQUENCE: 1

Met Arg Val Leu Leu Val Glu Asp Asp Ala Met Ile Ala Glu Ala Val

```
                1               5                   10                  15
Ser Ala Ser Leu Lys Asp Gly Gly Tyr Ala Val Asp Trp Val Lys Asn
                    20                  25                  30

Gly Ala Arg Leu Pro Leu Pro Ser Leu Met Thr Ala Ala Ala Ala Ala
                    35                  40                  45

Gln Pro Tyr Asp Leu Met Leu Leu Asp Leu Gly Leu Leu Gly Arg Asp
        50                  55                  60

Gly Leu Asp Val Met Phe Val Pro Leu
 65                  70
```

<210> SEQ ID NO 2
<211> LENGTH: 13
<212> TYPE: PRT
<213> ORGANISM: Neisseria gonorrhoeae

<400> SEQUENCE: 2

```
Met Arg Val Leu Leu Val Glu Asp Asp Ala Met Ile Ala
 1               5                  10
```

<210> SEQ ID NO 3
<211> LENGTH: 210
<212> TYPE: PRT
<213> ORGANISM: Neisseria gonorrhoeae

<400> SEQUENCE: 3

```
Ala Val Ser Ala Ser Leu Lys Asp Gly Gly Tyr Ala Val Asp Trp Val
 1               5                  10                  15

Lys Asn Gly Ala Gln Val Ala Ala Ala Ala Ala Gln Pro Tyr Asp
                    20                  25                  30

Leu Met Leu Leu Asp Leu Gly Leu Pro Gly Arg Asp Gly Leu Asp Val
                    35                  40                  45

Leu Ser Glu Ile Arg Ala Ala Gly Cys Thr Val Pro Val Leu Ile Val
        50                  55                  60

Thr Ala Arg Asp Asp Leu Tyr Ser Arg Leu Asn Gly Leu Asp Gly Gly
 65                  70                  75                  80

Ala Asp Asp Tyr Ile Val Lys Pro Phe Asp Met Ala Glu Phe Lys Ala
                    85                  90                  95

Arg Met Arg Ala Val Leu Arg Arg Gly Ser Gly Gln Ala Gln Ala Cys
                    100                 105                 110

Leu Ser Asn Gly Ala Leu Ser Leu Asn Pro Ala Thr Tyr Gln Val Glu
            115                 120                 125

Ile Ile Ala Glu Gly Arg Gln Val Ala Leu Ser Asn Gln Glu Phe Ser
    130                 135                 140

Val Leu Gln Ala Leu Leu Ala Arg Pro Gly Val Ile Leu Ser Arg Ser
145                 150                 155                 160

Asp Ser Glu Asp Lys Val Tyr Gly Trp Gly Glu Val Glu Ser Asn
                    165                 170                 175

Ala Val Asp Phe Leu Ile His Gly Leu Cys Lys Lys Leu Gly Lys Glu
                    180                 185                 190

Ser Ile Gln Asn Val Arg Gly Val Gly Trp Leu Met Pro Arg Gln Asp
            195                 200                 205

Ala Val
    210
```

<210> SEQ ID NO 4
<211> LENGTH: 222
<212> TYPE: PRT

<213> ORGANISM: Neisseria cinerea

<400> SEQUENCE: 4

Met Arg Val Leu Leu Val Glu Asp Asp Ala Met Ile Ala Glu Ala Val
1               5                   10                  15

Ser Ala Asn Leu Lys Asp Gly Gly Tyr Ala Val Asp Trp Val Lys Asn
            20                  25                  30

Gly Ala Gln Val Ala Ala Ala Ala Ala Gln Pro Tyr Asp Leu Met
        35                  40                  45

Leu Leu Asp Leu Gly Leu Pro Gly Arg Asp Gly Leu Asp Val Leu Ser
50                  55                  60

Glu Ile Arg Ala Ala Gly Cys Thr Val Pro Val Leu Ile Val Thr Ala
65                  70                  75                  80

Arg Asp Asp Leu Tyr Ser Arg Leu Asn Gly Leu Asp Gly Gly Ala Asp
                85                  90                  95

Asp Tyr Ile Val Lys Pro Phe Asp Met Ala Glu Leu Lys Ala Arg Met
            100                 105                 110

Arg Ala Val Leu Arg Arg Gly Ser Gly Gln Ala Gln Ala Cys Leu Ser
        115                 120                 125

Asn Gly Ala Leu Ser Leu Asn Pro Ala Thr Tyr Gln Val Glu Ile Ile
130                 135                 140

Ala Glu Arg Arg Gln Val Ala Leu Ser Asn Lys Glu Phe Ala Val Leu
145                 150                 155                 160

Gln Ala Leu Leu Ala Arg Pro Gly Val Ile Leu Ser Arg Ser Asp Leu
                165                 170                 175

Glu Asp Lys Ile Tyr Gly Trp Gly Ala Glu Val Glu Ser Asn Ala Val
            180                 185                 190

Asp Phe Leu Ile His Ala Leu Arg Lys Lys Leu Gly Lys Glu Asn Ile
        195                 200                 205

Gln Asn Val Arg Gly Val Gly Trp Leu Val Pro Gly Ala Val
210                 215                 220

<210> SEQ ID NO 5
<211> LENGTH: 416
<212> TYPE: PRT
<213> ORGANISM: Neisseria meningitidis

<400> SEQUENCE: 5

Met Phe Val Pro Leu Ala Met Leu Ala Gly Met Phe Ser Tyr Tyr Glu
1               5                   10                  15

Thr Phe His Glu Thr Glu Ala Leu Gln Asp Asp Leu Leu Arg Gln Ala
            20                  25                  30

Ala Leu Tyr Val Ala Pro Asp Ser Lys Pro Glu Thr Leu Pro Glu Gly
        35                  40                  45

Asp Gly Asp Thr Arg Ile Phe Val Gln Met Pro Gln Gln Glu Asp Pro
    50                  55                  60

Val Val Ser Leu Pro Ala His Leu Ala Asp Gly Leu His Thr Leu Gln
65                  70                  75                  80

Ala Asp Gly Asp Asp Tyr Tyr Arg Val Tyr Ile Arg Thr Thr Glu
                85                  90                  95

Gln Gly Arg Ile Ala Val Met Gln Glu Asn Glu Tyr Arg Glu Asp Leu
            100                 105                 110

Ala Ala Asp Ala Ala Arg Gln Ser Val Leu Pro Leu Leu Ala Ala Leu
        115                 120                 125

Pro Leu Met Ile Leu Leu Thr Val Trp Ile Thr His Lys Ala Met Arg

-continued

```
                130                 135                 140
Pro Val Arg Lys Leu Ser Gln Ser Leu Glu Gln Arg Ile Asn Asp
145                 150                 155                 160

Leu Ser Ala Leu Ser Val Asp Asn Ile Pro Ser Glu Ile Arg Gly Phe
                165                 170                 175

Val Thr Ala Ile Asn Leu Leu Lys Arg Ala Asp Glu Asp Ile Arg
                180                 185                 190

His Arg Gln Arg Phe Val Ala Asp Ala Ala His Glu Leu Arg Thr Pro
                195                 200                 205

Met Thr Ala Leu Ser Leu Gln Ala Glu Arg Leu Asn Asn Met Ser Leu
210                 215                 220

Pro Pro Asp Ala Ala Arg Gln Pro Ala Val Leu Gln Gln Ser Ile Arg
225                 230                 235                 240

Arg Asn Lys His Leu Leu Glu Gln Leu Leu Ala Leu Ala Arg Ser Gln
                245                 250                 255

Ser Asp Glu Thr Pro Leu Thr Lys Thr Thr Phe Gly Leu Gln Ser Arg
                260                 265                 270

Phe Arg Gln Val Leu Gln Glu Leu Met Pro Leu Ala Leu Glu Lys Arg
                275                 280                 285

Gln Asp Ile Gly Val Ala Val Gly Gly Asp Val Glu Val Ser Ala Asp
                290                 295                 300

Glu Thr Glu Ile Tyr Thr Leu Ile Lys Thr Phe Ala Asp Asn Ala Val
305                 310                 315                 320

Arg Tyr Thr Pro Pro Glu Gly Arg Ile Asp Leu Gly Phe Thr Asp Glu
                325                 330                 335

Gly Lys Tyr Leu Ala Val Trp Val Glu Asp Asn Gly Asn Gly Ile Pro
                340                 345                 350

Glu Ser Glu Arg Ala Arg Val Leu Asp Pro Phe Tyr Arg Ile Leu Gly
                355                 360                 365

Thr Glu Gln Gln Gly Thr Gly Leu Gly Leu Ser Ile Ala Asp Thr Leu
                370                 375                 380

Ala Lys Lys Tyr Gly Gly His Leu Glu Leu Thr Asp Ser Arg Arg Phe
385                 390                 395                 400

Gly His Gly Leu Leu Ile Arg Ala Leu Leu Asp Lys Glu Thr Leu Lys
                405                 410                 415
```

<210> SEQ ID NO 6
<211> LENGTH: 439
<212> TYPE: PRT
<213> ORGANISM: Neisseria gonorrhoeae

<400> SEQUENCE: 6

```
Met Pro Asp Arg Phe Phe Lys Ile Leu Lys His Ser Leu Gln Val Arg
1               5                   10                  15

Ile Ser Leu Ala Leu Ile Trp Met Phe Val Pro Leu Ala Met Leu Ala
                20                  25                  30

Gly Met Phe Ser Tyr Tyr Glu Thr Phe His Glu Thr Glu Ala Leu Gln
                35                  40                  45

Asp Asp Leu Leu Arg Gln Ala Ala Leu Tyr Val Gly Pro Asp Ser Lys
                50                  55                  60

Ser Glu Thr Leu Pro Glu Gly Asp Gly Asp Thr Arg Ile Leu Val Gln
65              70                  75                  80

Met Pro Gln Gln Glu Asp Pro Val Val Ser Leu Pro Ala His Leu Ala
                85                  90                  95
```

```
Asp Gly Leu His Thr Leu Arg Ala Asp Gly Asp Asp Tyr Tyr Arg
            100                 105                 110

Ala Tyr Ile Arg Thr Thr Glu Gln Gly Arg Ile Ala Val Met Gln Glu
        115                 120                 125

Asn Glu Tyr Arg Glu Asp Leu Ala Glu Asp Ala Ala Arg Gln Ser Val
130                 135                 140

Leu Pro Leu Leu Ala Ala Leu Pro Leu Met Ile Leu Leu Thr Val Trp
145                 150                 155                 160

Ile Thr His Lys Ala Met Arg Pro Val Arg Lys Leu Ser Gln Ser Leu
                165                 170                 175

Glu Gln Arg Arg Ile Asn Gly Leu Pro Ala Leu Ser Val Tyr Asn Ile
            180                 185                 190

Pro Ser Glu Ile Arg Gly Phe Val Thr Ala Ile Asn Leu Leu Leu Lys
        195                 200                 205

Arg Val Asp Glu Asp Ile Arg Arg Gln Arg Phe Val Ala Asp Ala
210                 215                 220

Ala His Glu Leu Arg Thr Pro Met Thr Ala Leu Ser Leu Gln Ala Glu
225                 230                 235                 240

Arg Leu Asn Asn Met Pro Leu Pro Pro Asp Ala Gly Arg Gln Ser Ala
                245                 250                 255

Val Leu Gln Gln Ser Ile Arg Arg Asn Lys His Leu Leu Glu Gln Leu
            260                 265                 270

Leu Ala Leu Ala Arg Ser Gln Ser Asp Glu Pro Pro Leu Ala Lys Thr
        275                 280                 285

Thr Phe Gly Leu Gln Ser Arg Phe Arg Gln Val Leu Gln Glu Leu Met
290                 295                 300

Pro Leu Val Leu Glu Lys Arg Gln Asp Ile Gly Val Ala Val Gly Gly
305                 310                 315                 320

Asp Val Glu Val Ser Ala Asp Glu Thr Glu Ile Tyr Thr Leu Val Lys
                325                 330                 335

Thr Phe Ala Asp Asn Ala Val Arg Tyr Thr Pro Asn Gly Gly Arg Ile
            340                 345                 350

Asp Leu Gly Phe Thr Asp Glu Gly Lys Tyr Leu Ala Val Trp Val Glu
        355                 360                 365

Asp Asn Gly Asn Gly Ile Pro Glu Ser Glu Cys Ala Arg Val Leu Asp
370                 375                 380

Pro Phe Tyr Arg Ile Leu Gly Thr Glu Gln Gln Gly Ala Gly Leu Gly
385                 390                 395                 400

Leu Ser Ile Ala Asp Thr Leu Ala Lys Lys Tyr Gly Gly Tyr Leu Glu
                405                 410                 415

Leu Thr Asp Ser Arg Arg Phe His Gly Leu Leu Ile Arg Ala Leu
            420                 425                 430

Leu Asp Lys Glu Thr Leu Lys
        435

<210> SEQ ID NO 7
<211> LENGTH: 378
<212> TYPE: PRT
<213> ORGANISM: Neisseria cinerea

<400> SEQUENCE: 7

Met Leu Asn Arg Leu Ile Arg Met Leu Lys Gln Ser Leu Gln Val Arg
1               5                   10                  15

Ile Cys Ile Ala Leu Ile Leu Met Phe Leu Pro Leu Ala Met Val Ala
            20                  25                  30
```

Gly Val Phe Ser Tyr Tyr Asp Thr Phe His Glu Ala Glu Leu Gln
         35                  40                  45

Asp Asp Leu Leu Arg Gln Thr Ala Leu Tyr Val Gly Pro Asp Tyr His
 50                  55                  60

Pro Asp Ala Leu Pro Glu Gly Asp Gly Asp Thr Arg Ile Leu Val Gln
 65                  70                  75                  80

Met Pro Asp Gln Glu Pro Ile Val Ser Leu Pro Met His Leu Lys Asp
                 85                  90                  95

Gly Leu His Thr Leu Arg Ala Asp Glu Asp Asp Tyr Tyr Arg Val
             100                 105                 110

Tyr Ile Arg Thr Thr Gly Arg Gly Arg Ile Ala Val Met Gln Glu Asn
             115                 120                 125

Glu Tyr Arg Glu Asp Leu Ala Ala Asp Ala Ala Met Gln Ser Val Leu
         130                 135                 140

Pro Leu Leu Ala Ala Leu Pro Leu Ile Ile Leu Leu Thr Val Trp Ile
145                 150                 155                 160

Thr His Gln Ala Met Arg Pro Val Arg Ile Leu Ser Gln Asn Leu Glu
                 165                 170                 175

Gln Arg Arg Leu Asp Asp Leu Ser Ala Leu Asn Thr Asp Asn Ile Pro
             180                 185                 190

Ser Glu Ile Lys Gly Phe Val Thr Ala Ile Asn Leu Leu Leu Lys Arg
             195                 200                 205

Val Asp Glu Asp Ile Arg Arg Arg Gln Arg Phe Ile Ala Asp Ala Ala
210                 215                 220

His Glu Leu Arg Thr Pro Met Thr Ala Leu Ser Leu Gln Ala Glu Arg
225                 230                 235                 240

Leu Asn Asn Met Pro Leu Pro Pro Asp Ala Ala Arg Gln Ser Ala Val
                 245                 250                 255

Leu Gln Gln Ser Ile Arg Arg Asn Lys His Leu Leu Glu Gln Leu Leu
             260                 265                 270

Ala Leu Ala Arg Ser Gln Ser Asp Glu Thr Pro Leu Thr Lys Thr Thr
         275                 280                 285

Phe Gly Leu Gln Ser Arg Phe Arg Arg Val Leu Gln Glu Leu Met Pro
290                 295                 300

Leu Ala Leu Glu Lys Arg Gln Asp Ile Gly Val Ala Val Glu Gly Asp
305                 310                 315                 320

Phe Glu Ile Phe Ala Asp Glu Thr Glu Ile Tyr Thr Leu Val Lys Thr
                 325                 330                 335

Phe Val Asp Asn Ala Ile Arg Tyr Thr Pro Ser Glu Gly Arg Ile Asp
             340                 345                 350

Leu Gly Phe Thr Asp Glu Gly Lys Tyr Leu Ala Val Trp Val Glu Asp
         355                 360                 365

Asn Gly Lys Gly Ile Pro Glu Ser Glu Arg
370                 375

<210> SEQ ID NO 8
<211> LENGTH: 20
<212> TYPE: DNA
<213> ORGANISM: Neisseria gonorrhoeae

<400> SEQUENCE: 8
cctgtccgtg tgttgcaatc                                          20

<210> SEQ ID NO 9

```
-continued

<211> LENGTH: 20
<212> TYPE: DNA
<213> ORGANISM: Neisseria gonorrhoeae

<400> SEQUENCE: 9
ccgttcccgt tatcctccac                                                 20

<210> SEQ ID NO 10
<211> LENGTH: 43
<212> TYPE: PRT
<213> ORGANISM: Neisseria meningitidis

<400> SEQUENCE: 10

Met Arg Val Leu Leu Val Glu Asp Asp Ala Met Ile Ala Glu Ala Val
 1               5                  10                  15

Ser Ala Ser Leu Lys Asp Gly Gly Tyr Ala Val Asp Trp Val Lys Asn
             20                  25                  30

Gly Ala Arg Leu Pro Leu Pro Ser Leu Met Thr
         35                  40

<210> SEQ ID NO 11
<211> LENGTH: 67
<212> TYPE: PRT
<213> ORGANISM: Neisseria meningitidis

<400> SEQUENCE: 11

Met Arg Val Leu Leu Val Glu Asp Asp Ala Met Ile Ala Glu Ala Val
 1               5                  10                  15

Ser Ala Ser Leu Lys Asp Gly Gly Tyr Ala Val Asp Trp Val Lys Asn
             20                  25                  30

Gly Ala Arg Leu Pro Ala Ala Ala Ala Ala Gln Pro Tyr Asp Leu Met
         35                  40                  45

Leu Leu Asp Leu Gly Leu Leu Gly Arg Asp Gly Leu Asp Val Met Phe
     50                  55                  60

Val Pro Leu
65

SEQ ID NO 12
LENGTH: 5
TYPE: PRT
ORGANISM: Neisseria gonorrhoeae

<400> SEQUENCE: 12

Phe Val Pro Leu Ala
 1               5
```